(12) United States Patent
Clendenen et al.

(10) Patent No.: US 10,085,679 B2
(45) Date of Patent: Oct. 2, 2018

(54) SYSTEM AND METHOD FOR DETECTING VASCULAR CONTAMINATION BY SURGICAL ANESTHETIC USING NON-INVASIVE IR SPECTROPHOTOMETRY

(75) Inventors: Steven R. Clendenen, Pontevedra, FL (US); Clifton R. Haider, Rochester, MN (US); Barry K. Gilbert, Rochester, MN (US); Oliver William Spees, Elk Grove, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/128,694

(22) PCT Filed: Jun. 22, 2012

(86) PCT No.: PCT/US2012/043820
§ 371 (c)(1),
(2), (4) Date: Feb. 25, 2014

(87) PCT Pub. No.: WO2012/178064
PCT Pub. Date: Dec. 27, 2012

(65) Prior Publication Data
US 2014/0316225 A1 Oct. 23, 2014

Related U.S. Application Data

(60) Provisional application No. 61/500,232, filed on Jun. 23, 2011.

(51) Int. Cl.
*A61B 5/1455* (2006.01)
*A61K 49/00* (2006.01)
(Continued)

(52) U.S. Cl.
CPC ........ *A61B 5/14556* (2013.01); *A61B 5/1455* (2013.01); *A61B 5/14546* (2013.01);
(Continued)

(58) Field of Classification Search
CPC .............................. A61B 5/00; A61B 5/1455
(Continued)

(56) References Cited

U.S. PATENT DOCUMENTS

| 5,119,815 A | 6/1992 | Chance |
| 5,176,882 A | 1/1993 | Gray et al. |

(Continued)

FOREIGN PATENT DOCUMENTS

| JP | H0698890 A | 4/1994 |
| JP | 2002116140 A | 4/2002 |

(Continued)

OTHER PUBLICATIONS

Mitsuhashi et al. Usefulness of intraoperative fluorescence imaging to evaluate local anatomy in hepatobiliary surgery. 2008 J. Hepatobiliary Surg. 15:508-514.*

(Continued)

*Primary Examiner* — Patricia Park
*Assistant Examiner* — Patrick M Mehl (57) ABSTRACT

A system and method for detecting vascular contamination by surgical anesthetic using non-invasive IR spectrophotometry. One embodiment is a method for operating an instrument such as an enhanced pulse oximeter to monitor a patient receiving local anesthetic marked with dye that absorbs infrared light. Light is applied to and detected from tissue of the patient. A signal representative of the detected light is processed to derive patient oxygenation information. The detected light is also processed to derive information representative of the presence of the dye-marked anesthetic. The oxygenation information and the information represen- (Continued)

tative of the presence of anesthetic are displayed. The oxygenation monitoring and display and the anesthetic monitoring and display can occur separately or concurrently. Fluorescing dyes and fluorescence detection approaches are used for anesthetic detection in some embodiments. Other embodiments apply a sequence of light pulses and correlate the applied light pulse sequence to the detected signal to identify the presence of the dye-marked anesthetic.

17 Claims, 11 Drawing Sheets

(51) Int. Cl.
*A61B 5/00* (2006.01)
*A61B 5/145* (2006.01)
(52) U.S. Cl.
CPC .......... *A61B 5/4821* (2013.01); *A61B 5/6826* (2013.01); *A61B 5/743* (2013.01); *A61B 5/7405* (2013.01); *A61B 5/746* (2013.01); *A61K 49/0017* (2013.01)
(58) Field of Classification Search
USPC ........................................ 600/476, 473, 314
See application file for complete search history.

(56) References Cited

U.S. PATENT DOCUMENTS

| | | | |
|---|---|---|---|
| 5,402,779 A * | 4/1995 | Chen | A61B 17/3401 600/322 |
| 5,475,234 A | 12/1995 | Xu et al. | |
| 5,582,169 A | 12/1996 | Oda et al. | |
| 5,857,462 A | 1/1999 | Thomas et al. | |
| 6,253,097 B1 | 6/2001 | Aronow et al. | |
| 2008/0076992 A1 | 3/2008 | Hete et al. | |
| 2009/0163783 A1* | 6/2009 | Mannheimer et al. | ....... 600/306 |
| 2010/0081903 A1 | 4/2010 | Izzetoglu | |
| 2014/0316225 A1 | 10/2014 | Clendenen et al. | |
| 2015/0109617 A1 | 4/2015 | Gilbert et al. | |
| 2015/0119661 A1 | 4/2015 | Gilbert et al. | |

FOREIGN PATENT DOCUMENTS

| | | |
|---|---|---|
| WO | 2013165887 A1 | 11/2013 |
| WO | 2013165888 A2 | 11/2013 |

OTHER PUBLICATIONS

Wahl et al. Dead-time optimized time-correlated photon counting instrument with synchronized independent timing channels. 2007 Rev. Scientif.Instrument 78:033106-1-033106-6.*
Selander et al. Longitudinal spread of intraneurally injected local anesthetics. 1978 Acta Anaesth. Scand. 22:622-634.*
Corlu et al. 2007 Optics Express 15:6696-6716.*
Nagpal et al. 2011 Rajasthan J. Ophtalmology reference# RJO20110101 8 pages, publication date Jan. 1, 2011.*
International Search Report and Written Opinion issued in PCT/US2012/043820 dated Jan. 3, 2013, 9 pages.
Ladd, L.A. et al., "Central Effects Index—a semiquantitative method for the assessment of CNS toxicity of local anaesthetic agents in sheep", Journal of Pharmacological and Toxicological Methods 44 (2000) 467-476.
Singh, Parvinder et al., "Cardiovascular and Central Nervous System Toxicity of Local Anesthetics", Seminars in Anesthesia, Perioperative Medicine and Pain, vol. 17, No. 1 (March), 1998, pp. 18-23.
International Search Report and Written Opinion issued in PCT/US2013/038621, dated Oct. 14, 2013, 19 pages.
International Search Report and Written Opinion issued in PCT/US2013/038623, dated Oct. 23, 2013, 17 pages.

\* cited by examiner

Hypothetical reference signal without noise (no fluoresence)

Fig. 6A

Cross correlation reference signal without noise (no fluoresence)

SYSTEM AND METHOD FOR DETECTING VASCULAR CONTAMINATION BY SURGICAL ANESTHETIC USING NON-INVASIVE IR SPECTROPHOTOMETRY

TECHNICAL FIELD

The invention relates generally to systems and methods for monitoring the presence of local anesthesia in a patient's bloodstream.

BACKGROUND OF THE INVENTION

Local anesthesia is, in many cases, a superior means of pain control in avoiding the side effects of narcotic pain medication. Nerve blocks are commonly used for postoperative pain control as well as the primary anesthetic when the avoidance of general anesthesia is desired. The use of local anesthesia in this application renders an area insensitive to pain without affecting consciousness, speeding the detection of complications and patient recovery. However, when performing a nerve block, relatively large drug doses can be required to inhibit the nerve conduction to the surgical site. By way of example, injection volumes can be in the range of 20-40 cc. Unfortunately, as little as 1 cc of local anesthesia injected into an artery can cause seizure, and large intravascular local anesthesia injection will block the conduction system of the heart, possibly leading to cardiac arrest and death. Symptoms evidencing the onset of toxic anesthesia contamination include numbness of the tongue, lightheadedness and visual and auditory disturbances, and can occur at concentrations below 7.5 mcg/ml. Approximately 5 in 10,000 surgeries report severe complications caused by intravascular local anesthesia, but thousands of regional blocks are done every day.

There are very few tools available to anesthesiologists to protect patients from this problem. One known method involves an epinephrine marked 'test dose' of local anesthesia. During injection doctors watch for an increase in heart rate or blood pressure indicating an inadvertent intravascular injection. Unfortunately, this method is very unreliable. Those taking beta blockers or wearing a pacemaker may be unresponsive to epinephrine. Children often have blocks done under general anesthesia which alters the body's response to adrenaline and makes it difficult to determine if the local anesthesia is intravascular. An epinephrine marker during an epidural can cause complications by decreasing blood flow to the fetus in pregnant women. There remains, therefore, a continuing need for improved systems and methods for providing accurate and early warning of intravascular local anesthesia.

SUMMARY OF THE INVENTION

One embodiment of the invention is a method for operating a spectrophotometer to monitor a patient receiving local anesthetic marked with dye that absorbs infrared light. This method includes: (1) applying light pulses to a patient receiving anesthetic marked with fluorescing dye; (2) detecting the light emitted from the patient and providing a signal representative of the light detected; (3) processing the signal to derive information representative of the presence of dye-marked anesthetic; and (4) displaying the information representative of the presence of the dye-marked anesthetic as a function of the information representative of the fluorescence.

Variations on this embodiment include the use of a marking dye with detectable florescent properties.

Another embodiment of the invention is a method for operating a pulse oximeter to monitor a patient receiving local anesthetic marked with dye that absorbs infrared light. This method includes: (1) receiving a pulse oximeter signal from the patient; (2) processing the signal to derive patient oxygenation information; (3) displaying the patient oxygenation information; (4) processing the signal to derive information representative of the presence of dye-marked anesthetic; and (5) displaying the information representative of the presence of the dye-marked anesthetic, wherein the oxygenation monitoring and display function and the anesthetic monitoring and display function occur concurrently.

Variations of this embodiment of the invention include administering local anesthetic marked with the dye. The dye can be LI-COR IRDye 800 CW dye or Qdot 800 ITK dye. The dye can have a peak absorption and/or emission near 800 nm. Displaying the information representative of the presence of dye-marked anesthetic can include issuing an alarm and/or displaying quantitative information. The optical signal need not be derived from the arterial pulse.

Another embodiment of the invention is a spectrophotometric oximeter system. This system includes: (1) a light source and sensor; (2) a processing system coupled to the sensor for monitoring a light signal received from a patient and concurrently deriving patient oxygenation information and dye-marked anesthetic information; and (3) a display coupled to the processing system for displaying the patient oxygenation information and the dye-marked anesthetic information. Variations of this embodiment of the invention include a display that simultaneously displays the patient oxygenation information and the dye-marked anesthetic information. The display of dye-marked anesthetic can include an alarm and/or a quantitative display.

Yet another embodiment of the invention is anesthetic doped with LI-COR IRDye 800 CW dye or Qdot 800 ITK dye for use in connection with the inventions described above.

DETAILED DESCRIPTION

The invention is a system and method for detecting vascular contamination by local anesthetic through the use of infrared (IR) spectrophotometry. Components of the system include an IR spectrophotometer and an IR dye marker. An amount of the IR dye marker is included in local anesthetic administered to a patient. The presence of the IR dye marker in the patient's bloodstream is monitored by the IR spectrophotometer and used as an indication of vascular contamination of the anesthetic.

References throughout this specification to "one embodiment," "an embodiment," "a related embodiment," or similar language mean that a particular feature, structure, or characteristic described in connection with the referred-to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of this disclosure, taken on its own and in possible connection with a figure, is intended to provide a complete description of all features of the invention. While the specification uses the term infrared (IR) spectrophotometry, it will be understood that the principles described herein apply to the full optical range.

Figure 1:
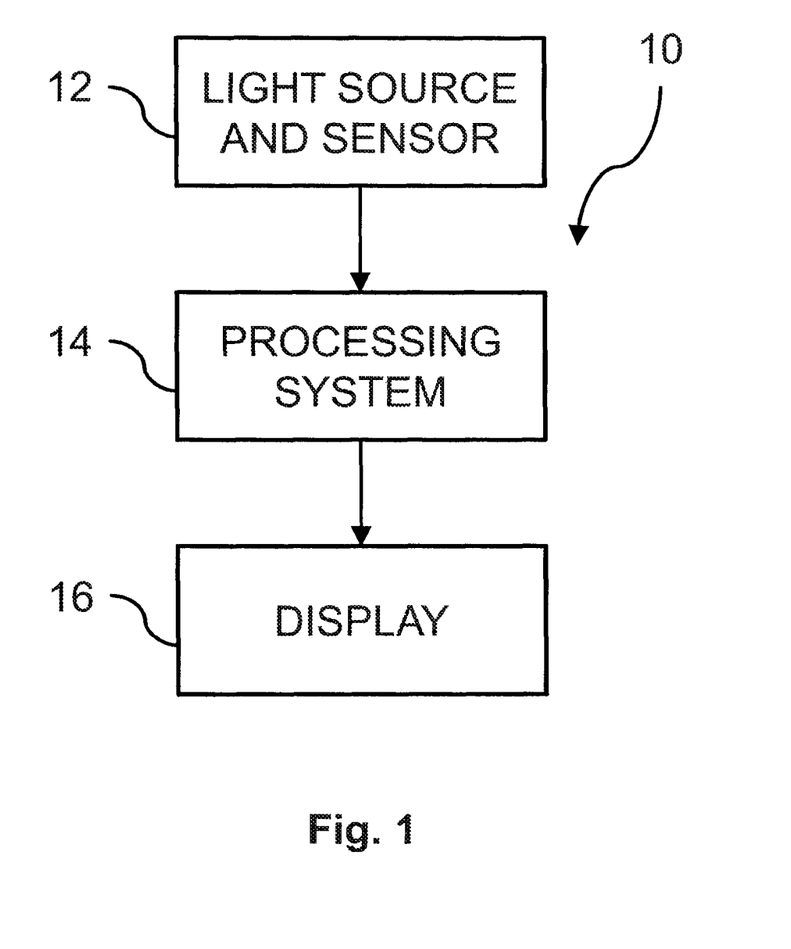
FIG. 1 is a block diagram of a spectrophotometer in accordance with one embodiment of the invention.

FIG. 1 is a block diagram of a spectrophotometer 10 that can be used in connection with the invention. As shown, spectrophotometer 10 includes a light source and sensor 12, processing system 14 and display 16. These components of spectrophotometer 10 are generally known and can be implemented in, e.g., the form of commercially available pulse oximeters. Light source and sensor 12 includes one or more lasers and one or more photodetectors (not separately shown) that are configured to direct light into the patient's tissue and to detect that light after it has passed through the tissue. Light source and sensor 12 are often configured to be mounted to the patient's finger or earlobe, but the mounting can take other forms, e.g. on the arm, as shown in FIG. 3B. Processing system 14 is coupled to the light source and sensor 12 and measures the baseline intensity of the detected light. Processing system 12 also detects absorbance (decrease in measured light) and fluorescence (increase in measured light) to identify the presence of the dye marker-doped local anesthesia in the vasculature. Information representative of the presence of detected local anesthesia can be shown on display 16 which can, for example, be a conventional surgical monitor or a monitor dedicated for anesthesia monitoring.

Pulse oximeters are important tools for monitoring patients' well being during and after surgery. Devices of this type utilize the difference in light absorbance of arterial and tissue/venous blood. This difference can be determined using two different frequencies such as 660 nm and 940 nm. Oxyhemoglobin and deoxyhemoglobin have an isosbestic point at 805 nm.

Absorption and scattering of light in the human body are largely a function of wavelength. Endogenous chromophores present in living tissue including hemoglobin, melanin and lipids absorb visible light and harmful UV light. However, infrared light passes through the human body several orders of magnitude more easily that UV light. Absorption and scattering decrease above 700 nm with an optical wavelength for imaging centered at 800 nm. Water increasingly absorbs light in the infrared spectrum, so dyes that fluoresce at wavelengths greater than 900 nm may see reduced signal-to-background noise ratios.

Sensitivity and limit of detection are important factors for the invention. A dye with a peak emission or absorption near 800 nm will enhance these factors. Interference with the function of pulse oximeters can be avoided if the dye absorbs and fluoresces at wavelengths between about 660 nm and 940 nm, or if all of the laser wavelengths are optimized together to yield best performance, simultaneously, for oximetry and for dye detection.

In general, dyes that can perform well with the present invention may have one or more of the following properties: (1) water soluble or conjugate to a biocompatible solvent such as polyethylene glycol, PBS or albumin, (2) fluoresce brightly with a strong signal-to-noise ratio (SNR), (3) physically pass through the body in a manner that does not frighten the patient, (4) do not affect pulse oximeter function with either peak absorption or emission near 800 nm, and (5) is FDA approved for clinical use.

One embodiment of the invention uses commercially available indocyanine green (ICG), a biocompatible Near-Infrared (NIF) fluorochrome. This dye is, for example, available from Scienceland.com of Houston Tex. ICG is FDA approved and has been used for years for medical imaging. Before surgery, a small amount of the patient's blood is drawn and spun to extract the serum. ICG binds readily to albumin. Once conjugated to the serum, the dye mixture is added to the injection of local anesthetic. If the dye is premixed with the local anesthetic to a standardized concentration, the ratio between detected dye emission/absorption and concentration of vascular anesthesia can be determined. In such a case display 16 could display real-time vascular concentration and be programmed to alarm given a sufficiently steep increase or at a threshold total concentration.

Spectrophotometer 10 can be configured to operate in several modes. Before injection of the anesthetic, a "Test Dose" mode can be selected, and a small (e.g., 1 cc) test dose of the marked drug is administered to test needle placement or nerve catheter placement. If the doped drug is injected directly into the blood stream, regardless of the injection's location, it will be distributed rapidly throughout the intravascular system and the spectrophotometer 10 will detect the dye and alarm the physician to stop the injection of local anesthetic. The physician can then reassess needle or nerve catheter placement. Threshold detection can sound a warning and/or prompt 'improper needle placement'. The physician can then reposition the needle and repeat test dose procedure.

Figure 2:
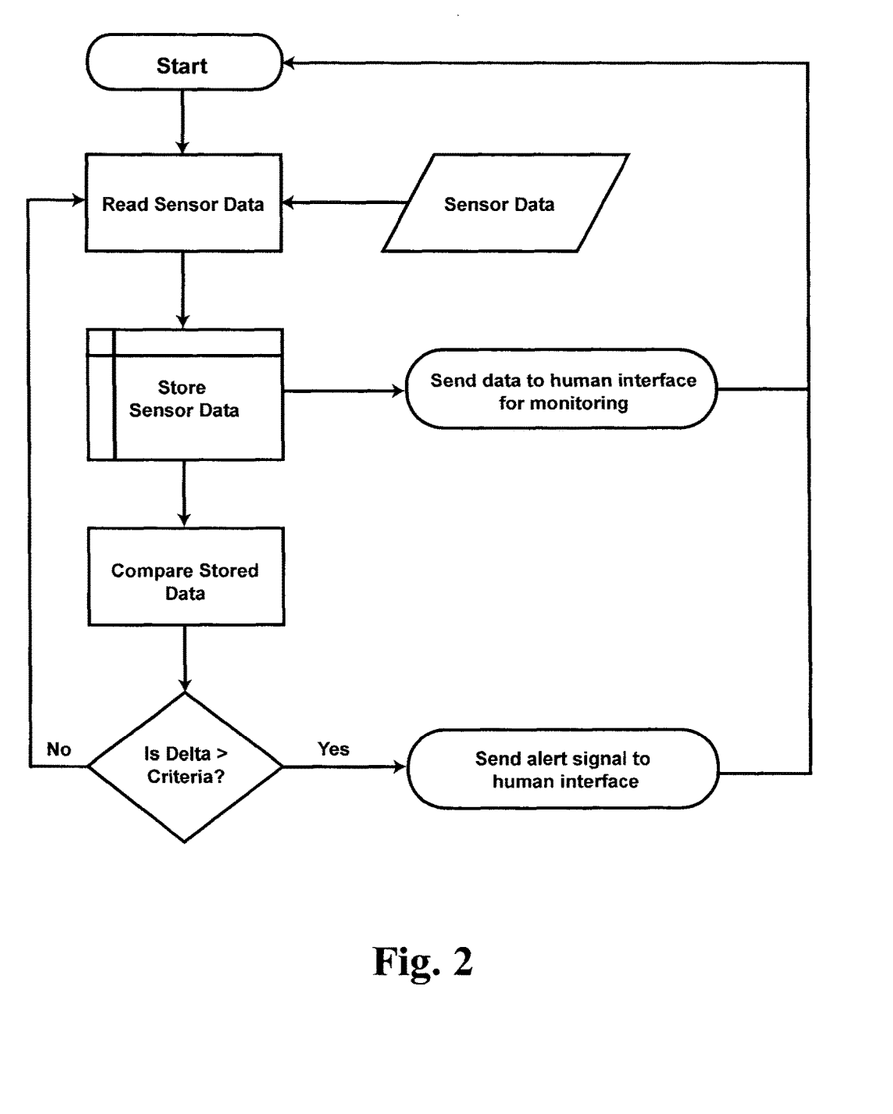
FIG. 2 is a flow diagram of an algorithm that can be implemented by the spectrophotometer shown in FIG. 1.

If the needle placement is accurate and local anesthetic is not detected within predefined tolerances after the test dose, a "Full Dose" mode can be selected for operation of the spectrophotometer 10, and the physician can slowly administer the full dose of local anesthetic or start the epidural catheter. In still other embodiments of the invention, the entire volume of local anesthetic (i.e., not just the test dose) is marked and detectable, and the spectrophotometer 10 is used for the duration of the procedure. The monitor will alarm the physician if the needle tip migrates into a blood vessel during the injection. In addition, infrequent cases such as catheter migration and extravasation when adjacent to large veins can also be detectable. After "Full Dose" mode is selected, threshold detection will sound an emergency alarm and alert doctors to inject antidote for intravascular injection of local anesthesia, e.g., a currently used antidote 'lipid rescue'. FIG. 2 is a flow diagram of a processing algorithm that can be implemented by processing system 14 of spectrophotometer 10 to derive information representative of the presence of dye-marked anesthetic in the bloodstream, and to issue alarms or otherwise display the monitored information.

Other example dyes that can be used in connection with the invention are IRDye 800CW available from LI-COR of Lincoln, Nebr. and Qdot 800 ITK available from Invitrogen of Carlsbad, Calif. IRDye 800CW-N-Carboxolate dye can be specifically conjugated to any number of biocompatible solvents including polyethylene glycol which would allow doctors early warning from local anesthesia extravasation from the surgical site. It is also significantly brighter than ICG, effectively lowering the limit of detection. Qdot 800 ITK dye includes tiny biocompatible nanocrystals (2-10 nm) and can be ordered preconjugated.

Figure 3A:
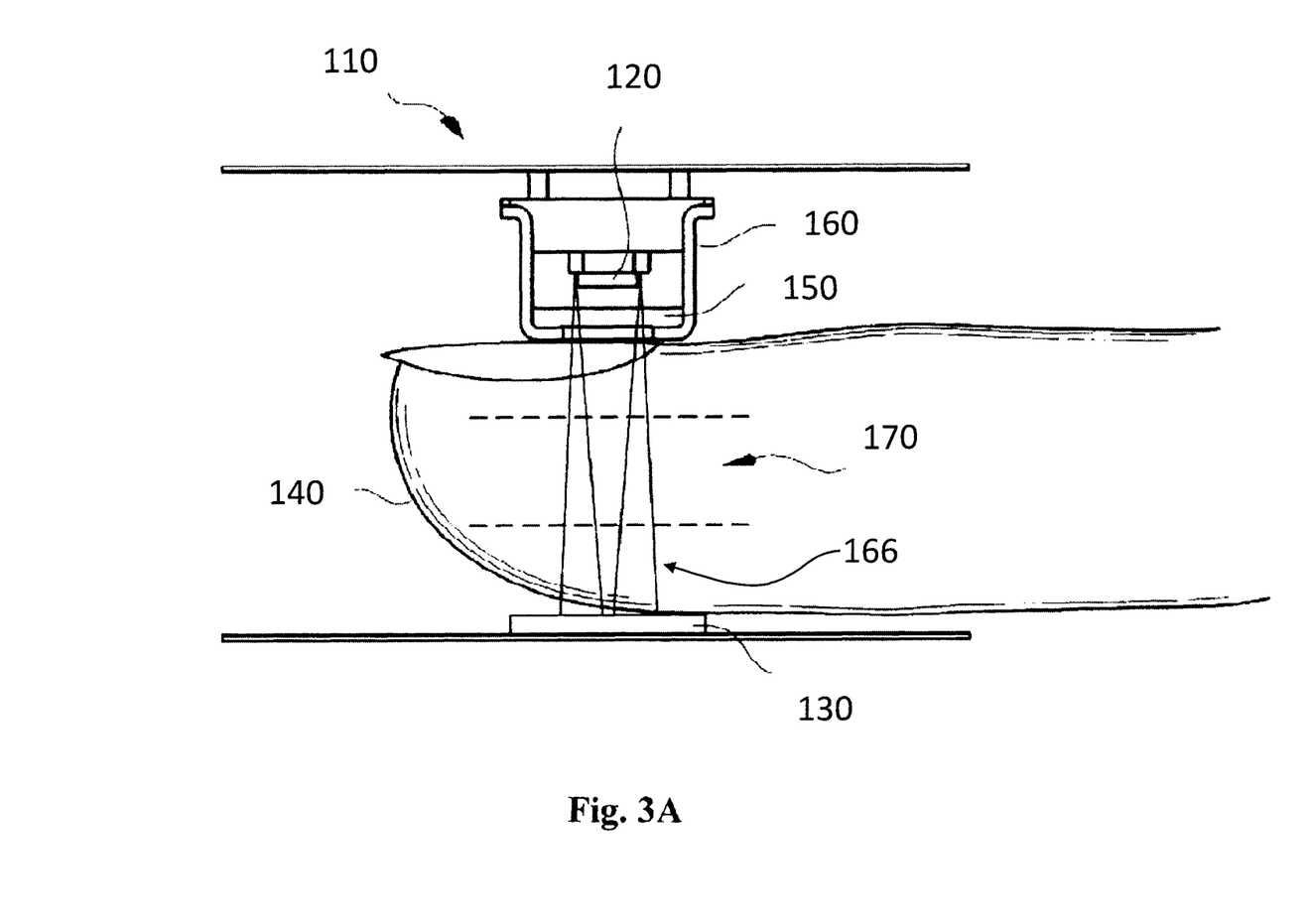
FIGS. 3A and 3B illustrate embodiments of a probe module that can be used in connection with the invention.
Figure 3B:
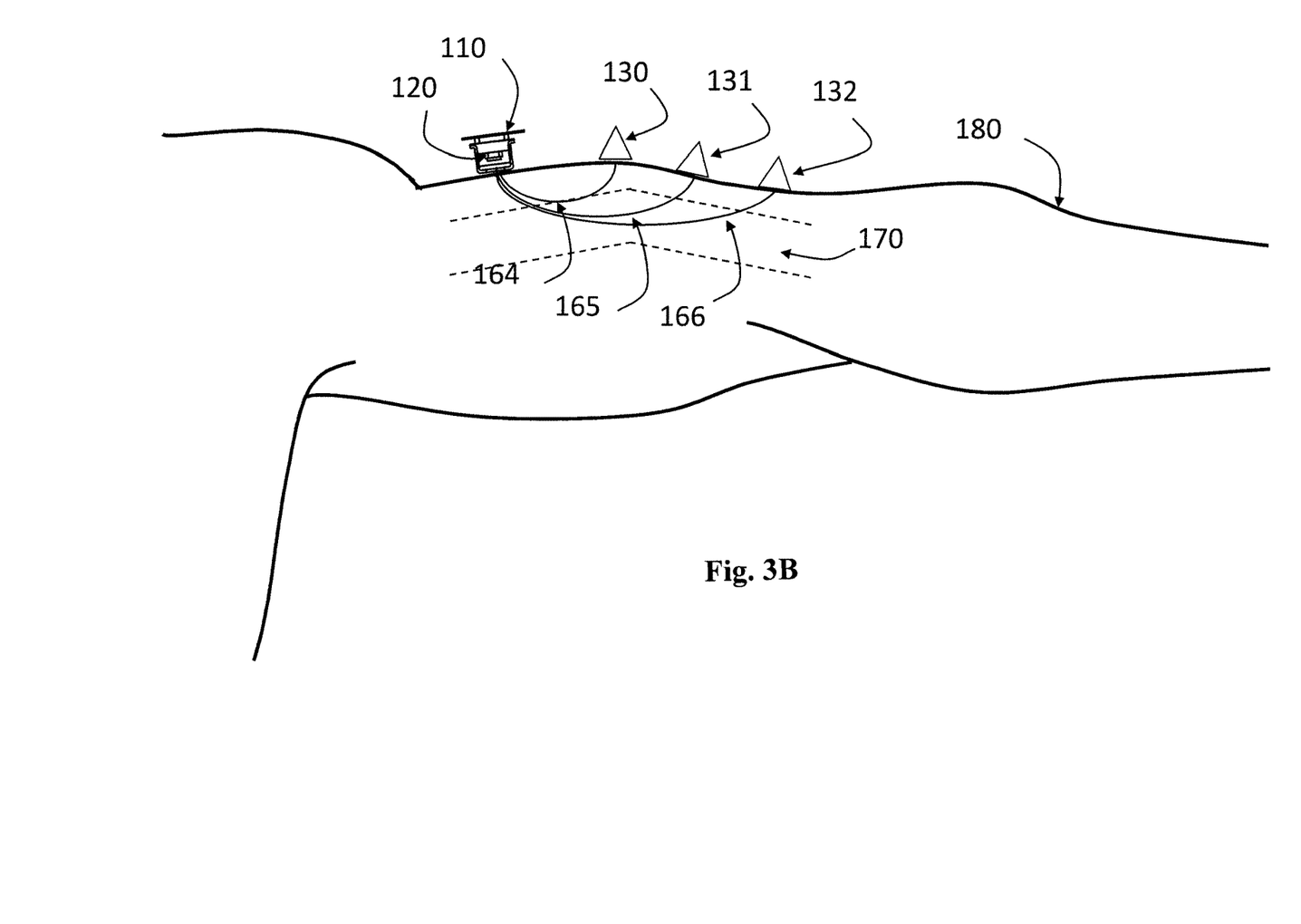

FIGS. 3A and 3B illustrate embodiments of a probe module 110 that can be used in connection with the invention. The probe module 110 contains one or more vertical cavity surface emitting lasers (VCSELs) 120, optionally spatially configured in a predetermined pattern or array. Each of the present VCSELs 120 generates a beam of light substantially centered at a selected wavelength, with at least one laser wavelength selected to emit at the frequency of excitation of the dye; or if the dye has more than one frequency of excitation, lasers can be selected that stimulate fluorescence at more than one wavelength. The probe module 110 also contains a light detector 130 configured to receive fluorescent light emitted by the dye following excitation of the dye by the laser diode(s) 120. The light detector 130 may include at least one of any suitable detector component, such as a photomultiplier tube (PMT), an avalanche photodiode, and a PIN diode, for example, and in a specific case may include an array of detectors. The probe module 110 may also contain a connector (not shown) adapted to operably connect the probe module 110 with a cable (not shown) that interconnects the probe with a monitor (not shown in FIGS. 3A and 3B). Alternately, the probe may be battery-operated and completely self-contained, including a visible readout, and/or an audible warning tone, and/or a wireless transmission capability to other equipment. The probe module 110 is shown to be juxtaposed to the patient's perfused tissue 140 (shown as a finger in FIG. 3A, for illustration purposes only), and is adapted to operate either in the transmission mode with the array of laser diodes 120 on one side of the finger 140 and the light detector 130 on the other side of finger 140, or in the reflectance or backscatter mode (shown as an arm in FIG. 3B, for illustration purposes only) where all the elements 120, 130 are positioned on the same side of the perfused tissue 140. The array of laser diodes 120 may include a diffuser 150 held in place by a mount 160. The diffusion of the light output is to ensure that light 166 generated by the array of laser diode light emitting devices 120 is not spatially concentrated and cannot cause harmful effects if mistakenly redirected to the patient's eyes. The change in the path length of the light beams 166 as they pass through the arteriolar bed 170 is one, but not necessarily the only, figure of merit used for determination of the concentration of blood analytes. The close spacing of the laser diodes 120 in the array results in the plurality of light beams produced by the laser diodes traversing substantially a common path through the arteriolar bed 170, which improves the accuracy of the measurements.

Referring to FIG. 3B, the probe module 110 is juxtaposed to the patient's tissue 170 shown as an upper arm 180, and multiple light detectors 130 are arranged in an array along the same surface of the upper arm 180. Optical paths 164, 165, and 166 determined by propagation of light from the light source 120 to the light detectors 130, 131, and 132 respectively, may traverse substantially different depths of the tissue 170 and, possibly, the arteriolar bed. The light detectors can generally be positioned at predetermined distances one from another. In this case, an optical pulse wave propagating through the tissue 170 is separately detectable by the spatially separated light detectors 130, 131, and 132. The time differences in the optical pulse-based analyte composition data associated with light received by these detectors can be used to determine various characteristics of the status of the patient such as, for example, cardiac stroke volume and beat-to-beat variation of cardiac stroke volume.

As but a single example, the LI-COR IRDye 800CW can be used to "tag" lidocaine. This dye is known to fluoresce at 789 nanometers (nm) if excited with light at 774 nm (i.e., at about 800 nm), and can be detected as follows. The laser 120 is pulsed frequently (e.g., in some but not all embodiments with the highest possible optical power achievable with that VCSEL), where the duration of each light pulse may be in the range of less than one nanosecond (ns) to a few ns, and with the pulses repeated in a specific sequence. In the embodiment described below and illustrated in FIG. 4, for example, the pulses are generated in what appears to be a random sequence. The sequence is actually deterministic, having a predictable and repeating sequence of levels and intervals. The determined sequence of pulses comprises an excitation sequence, used to drive the VCSEL in a repeatable pattern. The varied distribution of pulses can be tailored to the specific detection application such that the characteristics of interest are enhanced. These excitation sequences are referred to herein as pseudorandom (PRN) or PRN-like sequences, although other, non-PRN sequences are also possible and can be substituted as the excitation sequence without loss of generality. VCSELs can be employed for this application but embodiments of the invention are not limited to VCSELs; for example, edge-emitting lasers could be employed. If any anesthetic such as lidocaine is present in the central circulation, it will be accompanied by the fluorescent dye. The dye, struck by laser light at 774 nm, will fluoresce at 789 nm. The photodetector 130 will detect the fluorescent light. The larger the amount of circulating lidocaine, and the higher the optical power generated by the laser 120, the greater will be the amount of fluorescence, and the larger the signal output from the photodetector 130.

It is optionally beneficial to place a narrow-window optical filter (not shown) in the optical path of photodetector 130 to remove the laser light (or other stray light) from the measurement. The filter may be alternately in-line and out-of-line with the sensor to provide sensitive distinction between the illuminating light and the fluorescent light. Similar techniques may be employed to limit the sensitivity of the detector to alternately include the primary illumination or only the light from the fluorescing dye.

Figure 4:
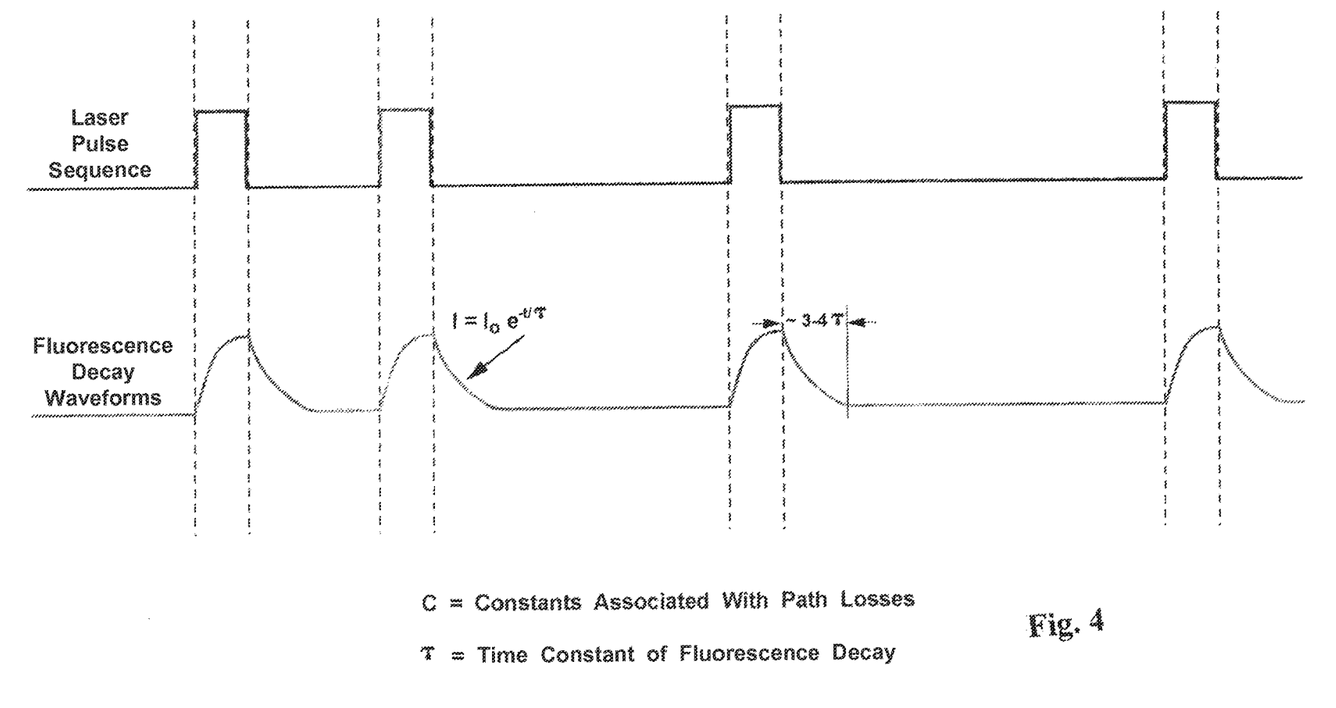
FIG. 4 is an illustration of laser pulses and fluorescence decay waveforms that can be produced in accordance with embodiments of the invention.

Another factor that can be accommodated by embodiments of the invention is that the decay time constant of the fluorescent light may be in the range of slightly less than one nanosecond (ns) to a few ns. The decay time constant for the LI-COR IRDye is, for example, in the range of 800 ps; however, other dyes or molecular "taggants" could have longer decay time constants and could alternately be employed with only minor changes to the design and implementation of the detection system. If the signal-to-noise ratio (SNR) is low in the fluorescent measurement, a selected excitation sequence can be used to dramatically improve the measurement of low concentrations of the fluorescing dye (of which small quantities are typically diluted into roughly five liters of blood). This approach works as follows in one embodiment of the invention: The laser is pulsed "on" and "off" using a specially designed or other sequence, where each "on" time is followed by an "off" time of specific length. One such possible sequence is a PRN sequence, though other non-PRN sequences could also be used. However, because the fluorescence decay time of the dye molecules may be as short as one ns or less, the sequence can be configured such that no "on"-pulse is followed by the next on-pulse by less than, e.g. but not limited to, 3-4 decay time constants, to allow the fluorescence signal to completely or substantially die away before the next "on"-pulse of the laser. A sequence of pulses having these features is illustrated in FIG. 4, for example.

In one embodiment the laser 120 is pulsed on and off in the manner described above using an electronic "clock" signal incorporated into the circuitry to "drive" the readout rate of the memory that stores the excitation sequence. The output from the sequence generator in turn drives the laser source to pulse or not pulse during any given clock cycle, depending on whether the stored pattern "requires" a laser pulse during that clock period or not; not every clock pulse results in a laser pulse, because for any given clock pulse the stored excitation pattern may not require a laser pulse. The selected clock frequency is advantageously approximately the inverse of the shortest laser pulse and approximately the same as one decay time constant of the dye. For example, for a dye with a 1 ns decay time constant, an appropriate system clock frequency might be 1 GHz. This same clock pulse stream is also fed to digital or analog processing circuitry "behind" the photodetector 130; that is, the analog electrical output signal from the photodetector is fed into the post-processing circuitry, referred to as a "cross correlator"; the cross correlator is driven by the clock pulse stream and also uses a copy of the stored excitation sequence to process the analog signal from the photodetector in a manner described below. Other embodiments of the invention include other approaches and structures for controlling the pulse sequence.

Figure 5:
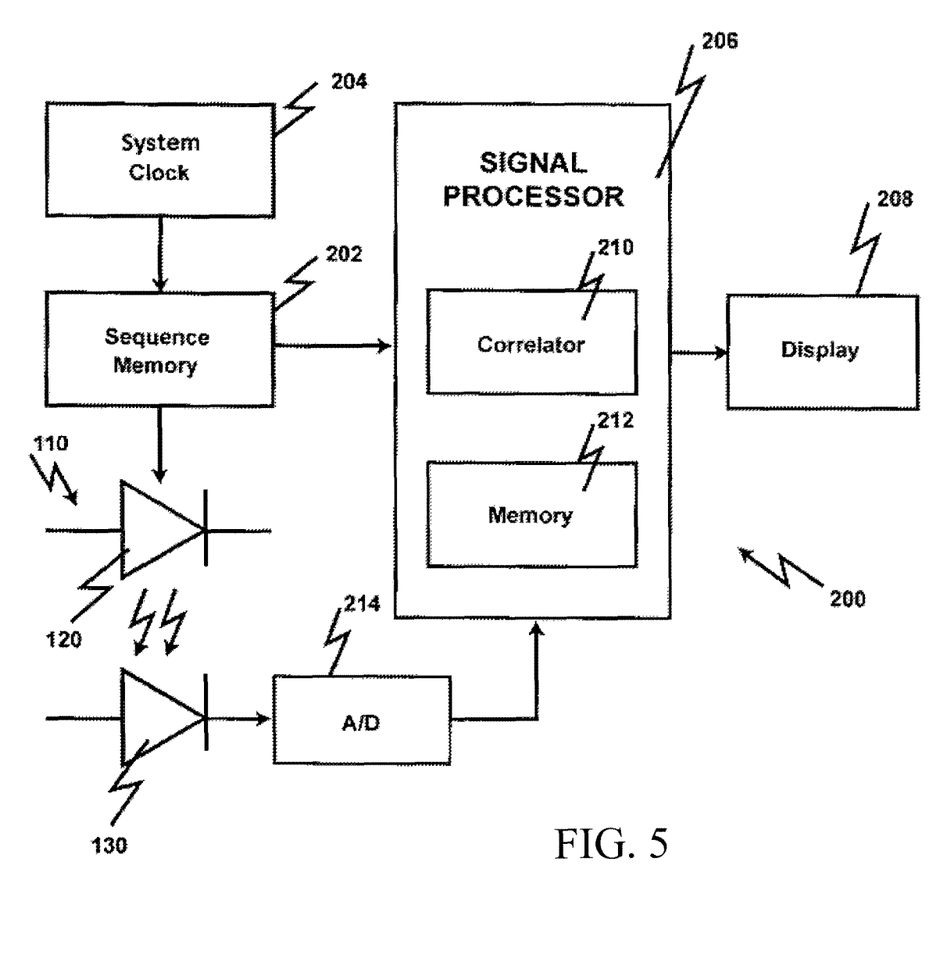
FIG. 5 is a block diagram of a monitor and display system in accordance with one embodiment of the invention.

FIG. 5 is a block diagram of a monitor and display system 200 in accordance with an embodiment of the invention connected to probe module 110. As shown, system 200 includes an excitation sequence memory 202 which stores the excitation sequence; the memory in turn is "read out" by the system clock 204, as noted above. The bit stream read out of the memory 212 is used to drive the laser 120 and also drive the signal processor 206, which contains the cross correlator 210 described above. Signal processor 206 includes correlator 210 and memory 212, and is coupled to display 208. The analog electrical signal from the photodetector 130 fed to the input of an analog-to-digital converter (A/D) 214, and the digital output stream from the A/D is fed to the input of the cross correlator 210 inside signal processor 206.

At least in part because the system 200 may need to detect very small concentrations of anesthetic and dye in a relatively large volume of blood (e.g., concentrations below 7.5 mcg/ml in some embodiments, and below 3.5 mcg/ml in other embodiments), SNR is important. Accordingly, levels of optical power exceeding 1 mW "eye-safe" levels can be considered, e.g., 5 mW. Most lasers such as but not limited to VCSELs can generate more than the eye-safe 1 mW levels, but care should be taken. In one embodiment of the invention (not shown), components (e.g., sensors) and circuitry are incorporated into the system such that the laser is electrically "turned off" unless the entire system is in direct contact with the patient's skin. The sensing function may be resistive (as in galvanic skin response measurements), capacitive (sensing the dielectric constant of the skin itself), or optical, or other approaches. When the circuitry detects skin contact, the laser is allowed to pulse at levels higher than eye-safe, but when there is no skin contact, the laser is turned off.

System 200 can process the analog signal from the photodetector 130 in the following manner. The approach is to "cross-correlate" the incoming electrical signal with the pre-established and known pattern used to "modulate", or pulse, the laser 120. The same clock signal used to control the pulsing of laser 120 by reading the excitation sequence from the sequence memory is fed to the signal processor 206 which can be, but need not be, incorporated into one or more silicon (or other material, such as a III-V compound semiconductor) integrated circuits. Cross correlator 210 may be an all-digital circuit. In other embodiments the correlator can be an analog cross-correlator. In the illustrated embodiment the correlator 210 is a digital implementation, and the output from the photodetector 130 is fed into the input of A/D 214. The analog signal is quantized in amplitude and time by A/D 214 to produce a stream of ones and zeros, or alternately, several-bit samples, depending on the details of implementation of the correlator 210. The correlator 210 employs the pre-established excitation sequence stored in memory 212 or may hold its own copy of the same excitation sequence, and as the digital samples "slide through" the correlator from its input to its output, the correlation process can take place in a known manner. The "output" from the correlator 210 is, almost at every "clock pulse", a low level digital electrical signal (or analog signal in analog embodiments), which becomes strong (typically for only one or a few clock pulse durations) when an exact or near-exact "match" is found between the stored excitation sequence and the incoming excitation sequence "embedded" in the analog electrical signal generated by the photodetector. As noted earlier, the "clock duration" (or inversely, the clock rate) of the entire system, including the readout rate from the excitation sequence memory and the step-by step operation of the correlator, can be in the same range as or shorter than one decay time constant of the dye (reference FIG. 4). If the decay time constant of the dye is 1 ns, then the system clock rate can be in the range of 1 GHz; if, for example, the decay time constant of the dye or taggant molecule were 10 ns, then the system clock rate can be in the range of 100 MHz or faster.

Typically, the output from correlator 210 in the general case is a voltage spike of only one or a few clock pulses in duration, with the shape of the pulse symmetric about its highest value. With all other design and operating parameters held constant, the amplitude of the central voltage spike is linearly proportional to the amount of signal recovered; thus a larger amplitude spike would, in this case, indicate a stronger recovered signal, and thus a higher amount of anesthetic-and-dye detected in the central circulation. "Signal processing gain" can be increased through the use of long excitation sequences, with the amount of signal processing gain roughly proportional to the square root of the number of "chips" in the applied excitation sequence, where a "chip" is the minimum duration of a "one" or "zero" in the code. Symmetric code sequences, that is, codes that contain an "odd" number of chips, and are symmetric about the central "one" bit, can be used to decrease the implementation complexity of the correlator by nearly a factor of two, without sacrificing signal processing gain.

The fluorescence also creates an identifiable change in the shape of the "typical" symmetric output pattern from the general usage case of a correlator. The "trailing edge" of the pulse is much longer than the "rising edge", which is a characteristic fingerprint for stimulated fluorescence as described above. The rising edge is related to the turn-on time of the laser, whereas the falling edge of the output pulse from the correlator is a convolution of the turnoff time of the laser with the decay time of the fluorescent light, possibly additionally modified by the transmission and scattering characteristics of the tissue. Merely the occurrence of the output spike from the correlator is sufficient to detect the presence of dye-tagged local anesthetic, but the additional feature of a non-symmetric output spike can be definitive for the presence of the dye molecule. Those skilled in the art will recognize that additional postprocessing of the output of the correlator 210 could be undertaken to further "key on" the asymmetric characteristics of the output pulse from the correlator. For example, curve-matching algorithms could be used, first, to identify the fact that the trailing edge of the output pulse from the correlator is longer in duration than the rising edge; second, if the decay time constant of the fluorescence is well characterized from laboratory measurements, the analysis could extend farther to show a "decay time-course match" between the output of the correlator and laboratory measurements, further "fingerprinting" the fact that fluorescence from the dye has been detected.

Figure 6A:
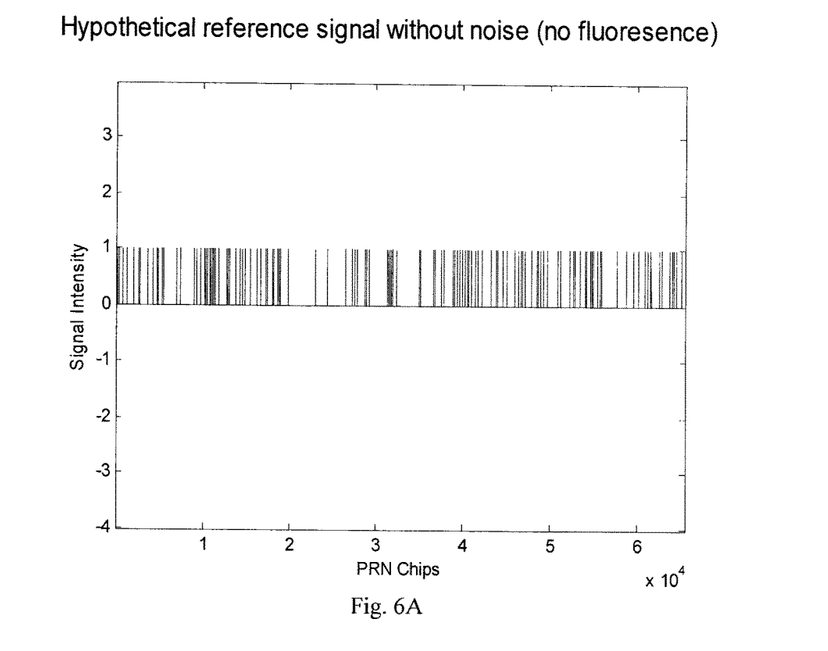
FIGS. 6A-6C are illustrations of a noise-free and fluorescence-free, pseudorandom excitation signal, a corresponding cross correlation output signal, and cross correlation output signal detail, respectively, in accordance with embodiments of the invention.
Figure 6B:
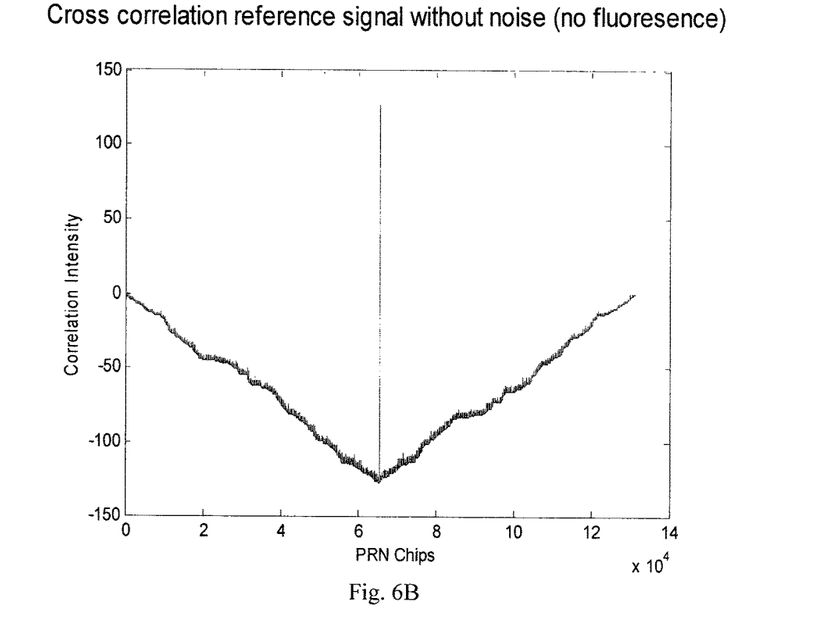
Figure 6C:
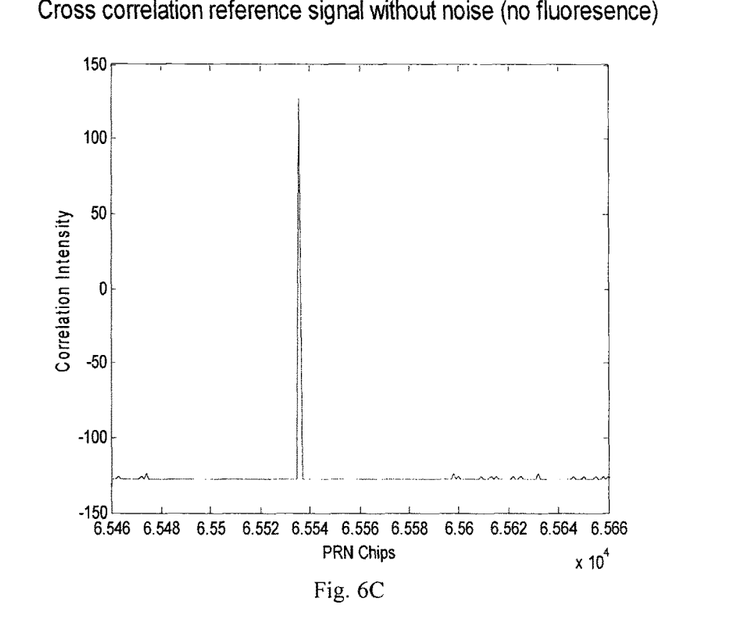
Figure 7A:
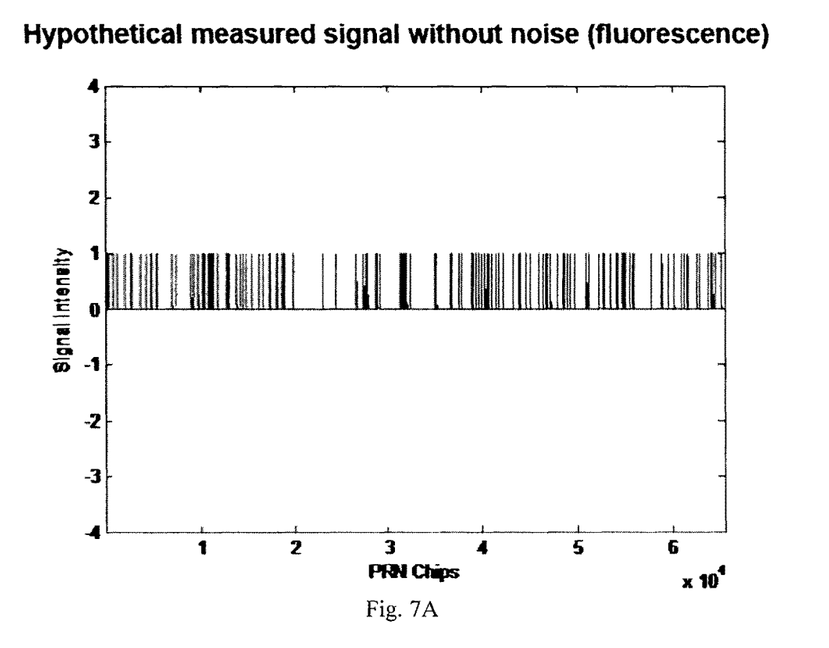
FIGS. 7A-7C are illustrations of a noise-free pseudorandom excitation signal in the presence of fluorescence, a corresponding cross correlation output signal, and cross correlation output signal detail, respectively, in accordance with embodiments of the invention.
Figure 7B:
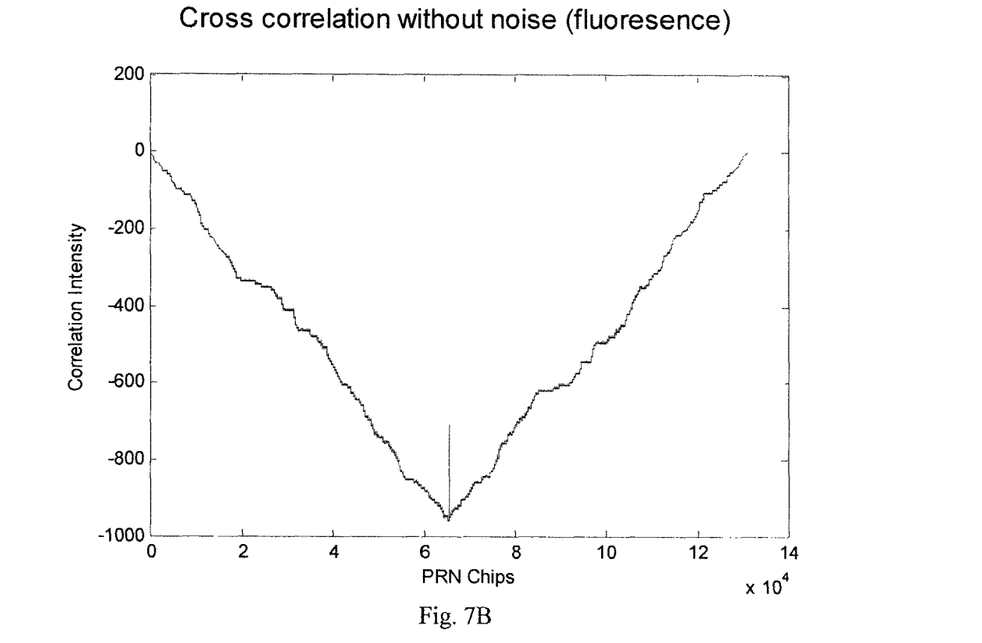
Figure 7C:
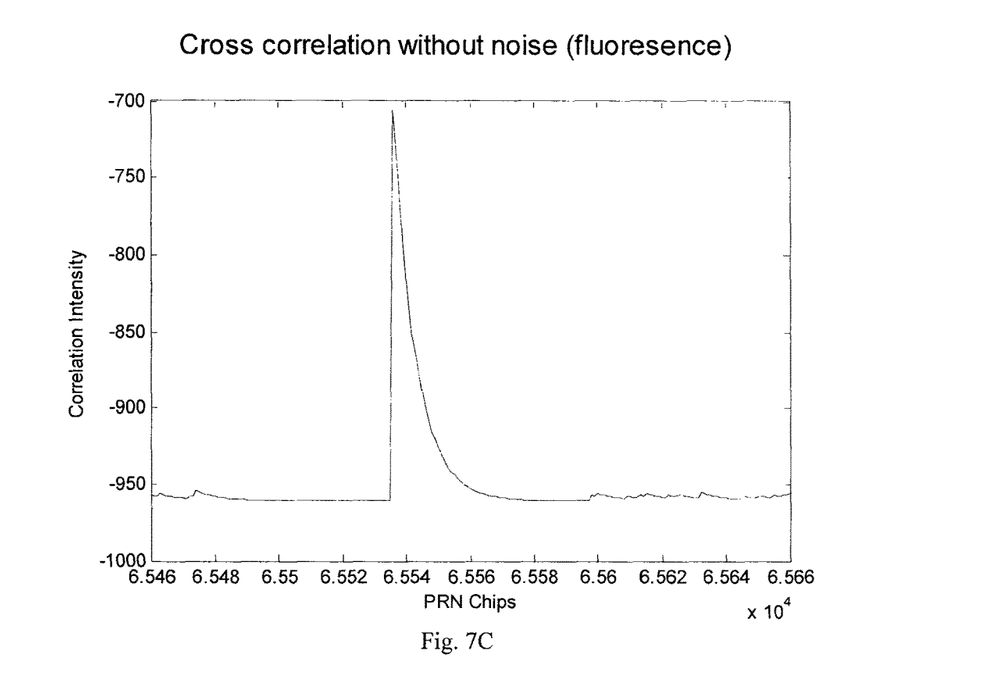
Figure 8A:
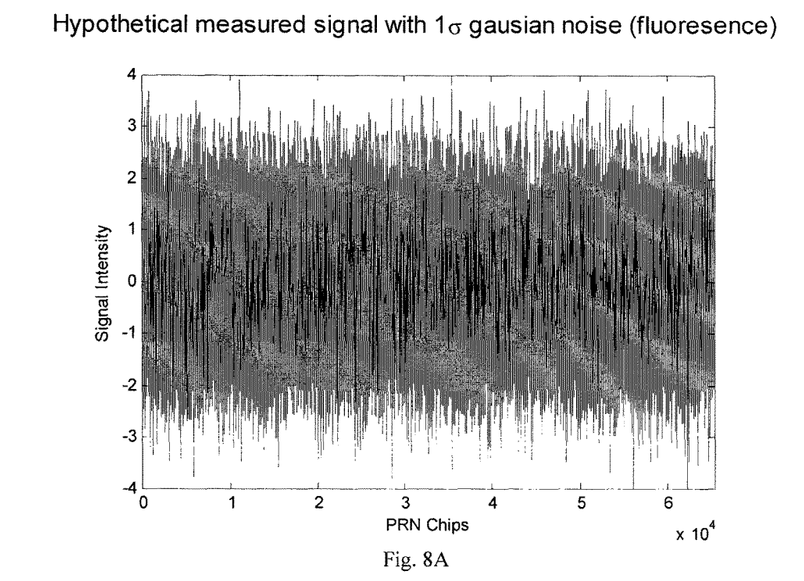
FIGS. 8A-8C are illustrations of a pseudorandom excitation signal in the presence of noise and fluorescence, a corresponding cross correlation output signal, and cross correlation output signal detail, respectively, in accordance with embodiments of the invention.
Figure 8B:
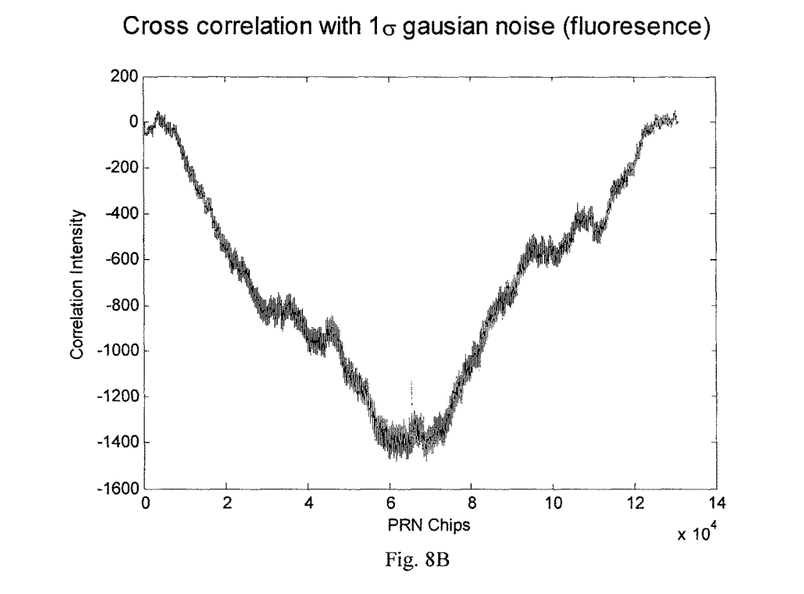
Figure 8C:
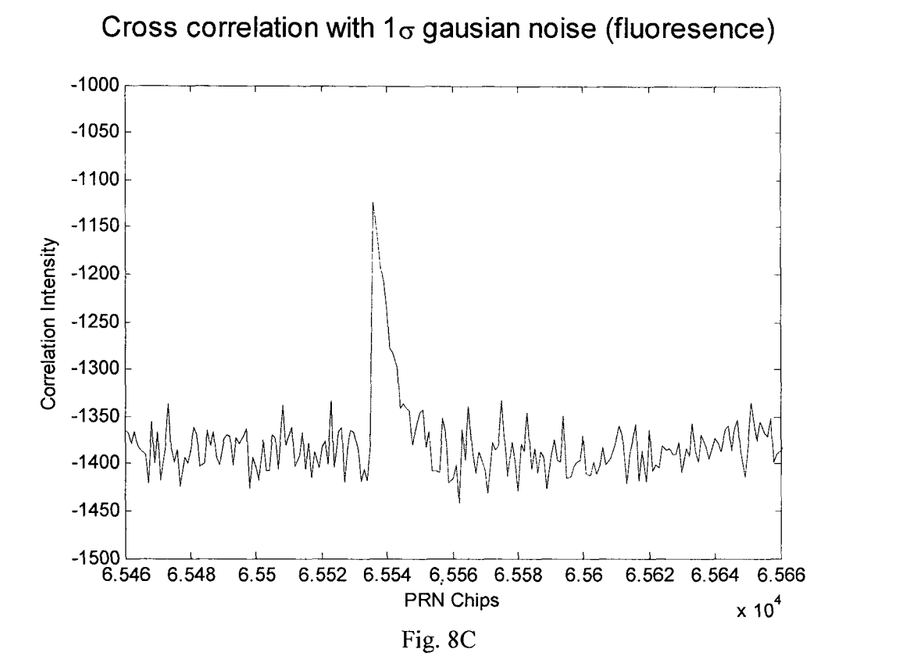

These operational features of the system 200 and the output signals produced by the correlator 210 can be described with reference to FIGS. 6A-6C, 7A-7C and 8A-8C. FIGS. 6A-6C illustrate the system 200 in connection with a reference material such as water with no noise or fluorescence. Specifically, FIG. 6A illustrates a noise-free and fluorescence-free example, wherein an excitation sequence drives the laser 120 and the same excitation sequence is used by the correlator 210 to carry out its correlation function. FIG. 6B illustrates the output signal produced by the correlator 210 when the system is driven by the signal shown in FIG. 6A. FIG. 6C is a detailed illustration of the correlation signal output spike shown in FIG. 6B. As is evident from FIG. 6C, since no fluorescence was present in the signal detected by the photodetector 130, the output spike is relatively large in amplitude, and does not include a decay feature (i.e., the rising and falling edges of equal slope and duration before and after the highest value of the output pulse. FIGS. 7A-7C illustrate the system operating in a noise-free environment and in the presence of fluorescent dye. The excitation sequence shown in FIG. 7A is similar to that shown in FIG. 6A. However, as is evident from FIG. 7C, the output spike from the correlator has a decay feature representative of the presence and detection of the dye-marked anesthetic in the monitored tissue of the patient, in that the trailing edge of the output pulse from the correlator is much longer in duration than is the rising edge of the output pulse. FIGS. 8A-8C illustrate the operation of the system in the presence of noise that would be typical of that expected in connection with the operation of system 200 in a real-world environment, in which system noise and other types of optical and electrical noise can be expected to be present. As shown in FIG. 8C, the output spike from the correlator 210, including the fluorescence-related decay feature, can be readily detected and identified even in a high-noise environment.

The use of PRN and similar excitation sequences provides important benefit to increase the sensitivity and specificity of the method implemented by the system 200 to the presence of the dye. For example, the use of the excitation sequence provides improved sensitivity to the presence of the fluorescence decay curve even in very low concentrations of the anesthetic and dye in the central circulation. The use of such excitation sequences have the benefit of the signal processing gain described above, but when dye detection is combined with oximetry, the use of multiple lasers at optimized frequencies, each driven by a unique excitation sequence, assist the process of measuring blood oxygen saturation and detection of anesthetic/dye in the central circulation. For example, the wavelengths employed for the oximetry function may not be directly in the emission or absorptive spectral regions of the dye, and therefore independent and simultaneous interrogation of the dye is possible without interference with the on-going pulse or quantitative oximeter measurements. In addition, wavelengths for the oximetry function can be optimized to decrease unwanted sensitivity to the presence of the dye, since another, or other, lasers are optimized to detect the dye; and all can function independently and simultaneously. Embodiments of the invention are capable of accurately identifying dye-marked anesthetic at concentrations below 7.5 mcg/1 m, and below 3.5 mcg/1 m, in the presence of system and environmental noise levels typically present in connection with oximeter-type instrumentation.

System 200 can record and store baseline measurements and use those measurements in connection with the removal of the effects of background fluorescence from unrelated and confounding sources, and remove the effects of other laser signals, improving the sensitivity to the desired fluorescent signal, i.e. to the presence of the dye. Alternatively, additional signal processing techniques, e.g. deconvolution and/or super resolution, are directly applicable to extract tissue effects from the fluorescent effect. The excitation sequence is intrinsically immune to fluctuations in the background, e.g. pulsatile blood flow, due to either very short duration sequences with nanosecond on and off times, or millisecond duration sequences, or long sequences that are over multiple cycles of, e.g. heart beats, to detect the presence of fluorescent dye.

If the system 200 detects the presence of fluorescence, display 208 can alert the attending physician or allied health professional by any one or more of several methods, e.g., but not limited to an audible tone, a quantitative readout built into the system such as an LED or LCD display, or the alert can be sent wirelessly to a monitoring console. Those skilled in the art will understand that a wide variety of alerting and monitoring mechanisms can be envisioned.

The dye detection function could be combined, through careful selection and optimization of multiple wavelengths, with the measurement of blood oxygen saturation as well, as noted above.

Similar embodiments to those described above can be used to detect and/or quantify naturally occurring biomolecules in the body whose chemical structures allow them to fluoresce if excited by the correct optical frequencies (i.e., they are naturally occurring fluorophores). Alternately, similar embodiments to those described above can be used to detect and/or quantify naturally occurring biomolecules that are not fluorophores but onto which other molecules can be chemically attached or bound, that in turn render the combined molecule fluorescent.

In summary, embodiments of the invention use a nontoxic fluorescing dye mixed with a local anesthetic such as lidocaine, bupivacaine, mepivacaine, ropivacaine, levobupivacaine and chloroprocaine to tag the presence of the anesthetic in the central circulation. The combination of a frequency-tuned VCSEL and enhanced selected excitation sequence to excite the fluorescence property of the dye, and the photo detector, is used to monitor the presence of the fluorescence. Any detected fluorescence can indicate that the anesthetic has entered the central circulation. Typically, the stronger the fluorescence signature, the more anesthetic has entered the central circulation. The system accounts for the fact that the fluorescence decay may last for only a few ns. Electro-optical "signal processing gain" is achieved by modulating the output of the laser ("on" and "off") with a specific known excitation sequence, such as a pseudorandom (PRN) sequence, which can be recovered from the electrical output signal from the photodetector using a real-time cross-correlation circuit. The effects of the fluorescent dye can be extracted with or without calibration.

The invention can rapidly detect intravascular injections of a local anesthetic laced with a dye caused by an incorrectly placed needle or catheter. This invention provides critical information to the anesthesiologist throughout the nerve block procedure. Not only will the system alert doctors when necessary, it will also help detail the blood level of dye-laced local anesthetic, providing quantitative data essential to provide appropriate therapy for treating patients suffering from accidental intravascular injections. The system can be incorporated into conventional pulse oximeters, and can be used in combination and at the same time as the functionality of the pulse oximeter if desired. Oximetry information and dye-marked anesthesia information can both be monitored and/or displayed simultaneously (i.e., concurrently or sequentially near in time). The spectrophotometer 10 can cause display 16 to show the monitored concentration levels of anesthetic and/or dye, and/or can issue an alarm if one or more thresholds of contamination are identified. This device can transform patient care by increasing patient safety during the infusion of local anesthesia, as a tool in early detection of accidental intravascular infusion of the local anesthesia caused by an incorrectly placed needle or catheter. This technology can also help monitor for drug error in which the nurse administers the drug in the incorrect catheter location, i.e., giving the local anesthesia into an intravenous catheter rather than a nerve catheter. This technology provides critical information which is currently unavailable to the anesthesiologist or only through test procedures known to be subjective and unreliable, converting such monitoring into a safer and quantifiable science.

Although the present invention has been described with reference to preferred embodiments, those skilled in the art will recognize that changes can be made in form and detail without departing from the spirit and scope of the invention.

The invention claimed is:

1. A method, comprising:
applying light from one or more sources to tissue of a patient, wherein the light has multiple wavelengths and includes pulses of light having an excitation wavelength and a predetermined excitation pulse sequence;
detecting the light by a light detector after the light has passed through the tissue of the patient, including detecting light having an emission wavelength that is different than the excitation wavelength;
processing the detected light by a processing system, including:
correlating pulse sequences of detected light having the emission wavelength with the predetermined excitation pulse sequence to identify the recovery of light having the emission wavelength, wherein the recovery of light having the emission wavelength is representative of the presence of fluorescing dye-marked anesthetic in the patient's bloodstream; and
processing the detected light to determine the blood oxygen saturation level of the patient; and
displaying concurrently the patient's blood oxygen saturation level, and information representative of the presence of dye-marked anesthetic in the patient's bloodstream based on the recovery of the light having the emission wavelength.

2. The method of claim 1 wherein displaying the information representative of the presence of the dye-marked anesthetic includes displaying one or more of audible information and visual information.

3. The method of claim 2 wherein the audible information includes an audible alarm.

4. The method of claim 2 wherein the visual information includes one or more of qualitative information and quantitative information representative of the amount of dye-marked anesthetic in the patient's bloodstream.

5. The method of claim 1 wherein applying light having the excitation wavelength and/or detecting light having the emission wavelength includes applying and/or detecting light having a wavelength of about 800 nanometers.

6. The method of claim 1 wherein:
applying light from one or more sources includes applying light having an oximetry wavelength different than the excitation and emission wavelengths; and
processing the light to determine the blood oxygen saturation level of the patient includes processing detected light having the oximetry wavelength.

7. The method of claim 1 wherein the predetermined excitation pulse sequence includes a sequence of pulses with different intervals between the pulses.

8. An instrument for use in connection with a patient receiving fluorescing dye-marked anesthetic, comprising:
a probe configured to be positioned on the patient, including:
a source of light having multiple wavelengths, including pulses of light having an excitation wavelength and a predetermined excitation pulse sequence; and
a detector for detecting light, including light having an emission wavelength that is different than the excitation wavelength;
a processing system coupled to the probe, wherein the processing system concurrently:
correlates detected pulse sequences of light having the emission wavelength with the predetermined excitation pulse sequence to identify the recovery of light having the emission wavelength, wherein the recovery of light having the emission wavelength is representative of the presence of the fluorescing dye-marked anesthetic in the patient's bloodstream; and
processing the detected light to determine the blood oxygen saturation level of the patient; and
a display coupled to the processing system to display the patient oxygenation information and information representative of the presence of the dye-marked anesthetic in the patient's bloodstream.

9. The instrument of claim 8 wherein the display concurrently displays the patient oxygenation information and the information representative of the presence of dye-marked anesthetic.

10. The instrument of claim 8 wherein the display simultaneously displays the patient oxygenation information and the information representative of the presence of dye-marked anesthetic.

11. The instrument claim 8 wherein the display displays one or more of audible information and visual information representative of the presence of dye-marked anesthetic.

12. The instrument of claim 11 wherein the display displays audible information including an audible alarm.

13. The instrument of claim 11 wherein the display displays visual information including one or more of qualitative information and quantitative information representative of the amount of dye-marked anesthetic in the patient's bloodstream.

14. The instrument of claim 8 wherein:
the processing system includes a clock signal that reads out the predetermined excitation pulse sequence from a memory, such that an output of the memory determines the excitation pulse sequence; and the same clock signal is used to correlate the detected light having the emission wavelength with the predetermined excitation pulse sequence.

15. The instrument of claim 8 wherein the probe further includes one or more devices to generate the light.

16. The instrument of claim 8 wherein:
the source of light having multiple wavelengths includes light having an oximetry wavelength different than the excitation and emission wavelengths; and
the processing system processes detected light having the oximetry wavelength to determine the blood oxygen saturation level of the patient.

17. The instrument of claim 8 wherein the predetermined excitation pulse sequence includes a sequence of pulses with different intervals between the pulses.

* * * * *